(12) United States Patent
Rock

(10) Patent No.: US 7,681,569 B2
(45) Date of Patent: Mar. 23, 2010

(54) MEDICAL LIQUID PROCESSOR APPARATUS AND METHOD

(75) Inventor: Kelly P. Rock, Henderson, NV (US)

(73) Assignee: LyteSyde, LLC, Miami Beach, FL (US)

( * ) Notice: Subject to any disclaimer, the term of this patent is extended or adjusted under 35 U.S.C. 154(b) by 1052 days.

(21) Appl. No.: 11/337,770

(22) Filed: Jan. 23, 2006

(65) Prior Publication Data

US 2007/0169773 A1 Jul. 26, 2007

(51) Int. Cl.
*A61M 11/00* (2006.01)
(52) U.S. Cl. .............................. 128/200.14; 128/200.18; 128/200.23
(58) Field of Classification Search ............ 128/200.11, 128/200.12, 200.13, 200.14, 200.18, 200.22, 128/203.15, 203.16, 203.19, 203.23; 239/399, 239/400, 402, 403, 405, 406, 409, 338; 261/78.2, 261/79.2
See application file for complete search history.

(56) References Cited

U.S. PATENT DOCUMENTS

| | | | |
|---|---|---|---|
| 634,242 A | 10/1899 | Lambert | |
| 751,292 A | 2/1904 | Johanson | |
| 860,259 A | 7/1907 | Smith | |
| 1,163,437 A | 12/1915 | Morison | |
| 1,233,557 A | 7/1917 | Curtis | |
| 1,309,719 A | 7/1919 | Curtis | |
| 1,313,521 A | 8/1919 | Connor et al. | |
| 1,451,063 A | 4/1923 | Anthony | |
| 1,471,220 A | 10/1923 | Tangye | |
| 1,626,085 A | 4/1927 | Henriot | |
| 2,071,717 A | 2/1937 | Winkle | |
| 2,599,422 A | 6/1952 | Yetlaw | |
| 3,286,997 A | 11/1966 | Ledbetter | |
| 3,336,017 A | 8/1967 | Kopa | |
| 3,395,899 A | 8/1968 | Kopa | |
| 3,414,242 A | 12/1968 | Bouteleux | |
| 3,506,589 A | 4/1970 | Hoffman et al. | |
| 3,515,676 A | 6/1970 | Hierta et al. | |
| 3,651,619 A | 3/1972 | Miura | |
| 3,667,221 A | 6/1972 | Taylor | |
| 3,733,060 A | 5/1973 | Merritt | |
| 3,761,065 A | 9/1973 | Rich et al. | |
| 3,778,038 A | 12/1973 | Eversole | |
| 3,811,278 A | 5/1974 | Taylor et al. | |
| 3,866,585 A | 2/1975 | Kopa | |
| 3,944,634 A | 3/1976 | Gerlach | |
| 3,946,552 A | 3/1976 | Weinstein et al. | |
| 3,972,182 A | 8/1976 | Salvi | |
| 4,030,283 A | 6/1977 | Sauthier et al. | |

(Continued)

FOREIGN PATENT DOCUMENTS

GB      2 296 037      6/1996

(Continued)

*Primary Examiner*—Justine R Yu
*Assistant Examiner*—Christopher Blizzard
(74) *Attorney, Agent, or Firm*—Holland & Hart

(57) ABSTRACT

Some embodiments and aspects presented herein provide methods and apparatus for vaporizing and/or mixing medication with air or other gases for oral delivery to a patient. Some methods and apparatus may include breaking liquid medications down to particle sizes no larger than about 1.0 to 3.0 micrometers in diameter. Such small particle diameters can be introduced directly to a patient's bloodstream via the lungs by crossing the alveoli membranes.

22 Claims, 4 Drawing Sheets

U.S. PATENT DOCUMENTS

| | | | |
|---|---|---|---|
| 4,087,862 A | 5/1978 | Tsien | |
| 4,159,881 A | 7/1979 | Gogneau | |
| 4,173,863 A | 11/1979 | Motoki et al. | |
| 4,178,134 A | 12/1979 | Babish et al. | |
| 4,185,453 A | 1/1980 | Jaunin | |
| 4,215,535 A | 8/1980 | Lewis | |
| 4,217,313 A | 8/1980 | Dmitrievsky et al. | |
| 4,218,020 A * | 8/1980 | Reider | 239/406 |
| 4,232,384 A | 11/1980 | Jaunin | |
| 4,245,338 A | 1/1981 | Sekiya et al. | |
| 4,255,410 A | 3/1981 | Spevack | |
| 4,261,048 A | 4/1981 | Motoki et al. | |
| 4,261,354 A | 4/1981 | Nelson | |
| 4,267,131 A | 5/1981 | Prudhon et al. | |
| 4,275,463 A | 6/1981 | Ishida | |
| 4,308,607 A | 12/1981 | Kopa | |
| 4,335,804 A | 6/1982 | Bardin et al. | |
| 4,452,239 A | 6/1984 | Malem | |
| 4,464,314 A | 8/1984 | Suroviken et al. | |
| 4,515,734 A | 5/1985 | Rock et al. | |
| 4,568,500 A | 2/1986 | Rock et al. | |
| 4,595,143 A * | 6/1986 | Simmons et al. | 239/406 |
| 4,635,857 A | 1/1987 | Hughes | |
| 4,726,686 A | 2/1988 | Wolf et al. | |
| 4,842,777 A | 6/1989 | Lamort | |
| 4,943,704 A | 7/1990 | Rabenau et al. | |
| 4,992,206 A | 2/1991 | Waldron | |
| 5,008,048 A | 4/1991 | Ryder | |
| 5,071,068 A | 12/1991 | Suniewski | |
| 5,169,302 A | 12/1992 | Keller | |
| 5,340,306 A | 8/1994 | Keller et al. | |
| 5,470,311 A * | 11/1995 | Setterstrom et al. | 604/24 |
| 5,472,645 A | 12/1995 | Rock et al. | |
| 5,476,093 A | 12/1995 | Lankinen | |
| 5,487,378 A | 1/1996 | Robertson et al. | |
| 5,512,216 A | 4/1996 | Rock et al. | |
| 5,529,059 A | 6/1996 | Armstrong et al. | |
| 5,672,187 A | 9/1997 | Rock et al. | |
| 5,687,710 A | 11/1997 | Ambrosio et al. | |
| 5,775,320 A | 7/1998 | Patton et al. | |
| 5,848,750 A | 12/1998 | Schwab | |
| 5,911,363 A * | 6/1999 | Oligschlaeger | 239/11 |
| 5,964,406 A * | 10/1999 | Zuo | 239/88 |
| 6,113,078 A | 9/2000 | Rock | |
| 6,234,459 B1 | 5/2001 | Rock | |
| 6,244,573 B1 | 6/2001 | Rock | |
| 6,669,176 B2 * | 12/2003 | Rock | 261/79.2 |
| 7,231,919 B2 * | 6/2007 | Giroux | 128/203.15 |

FOREIGN PATENT DOCUMENTS

SU          909429       *  2/1982

* cited by examiner

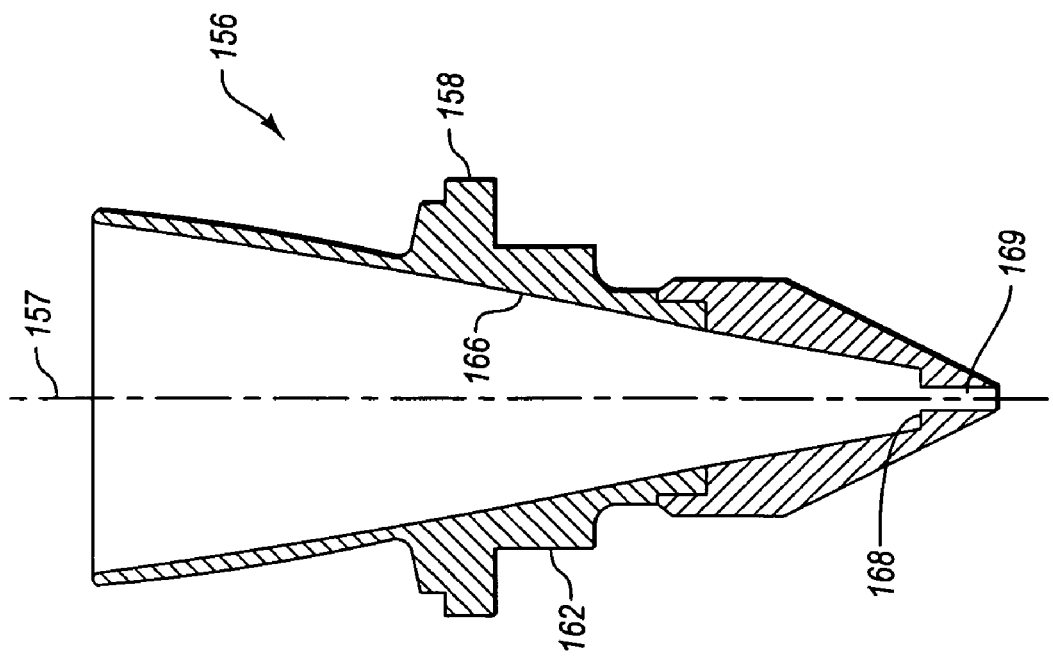
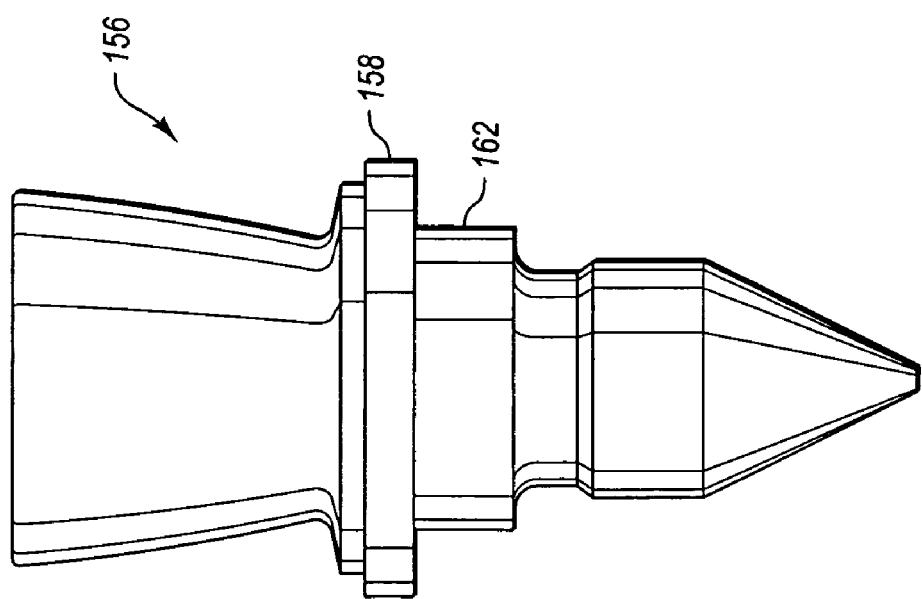
Fig. 2B
Fig. 2A

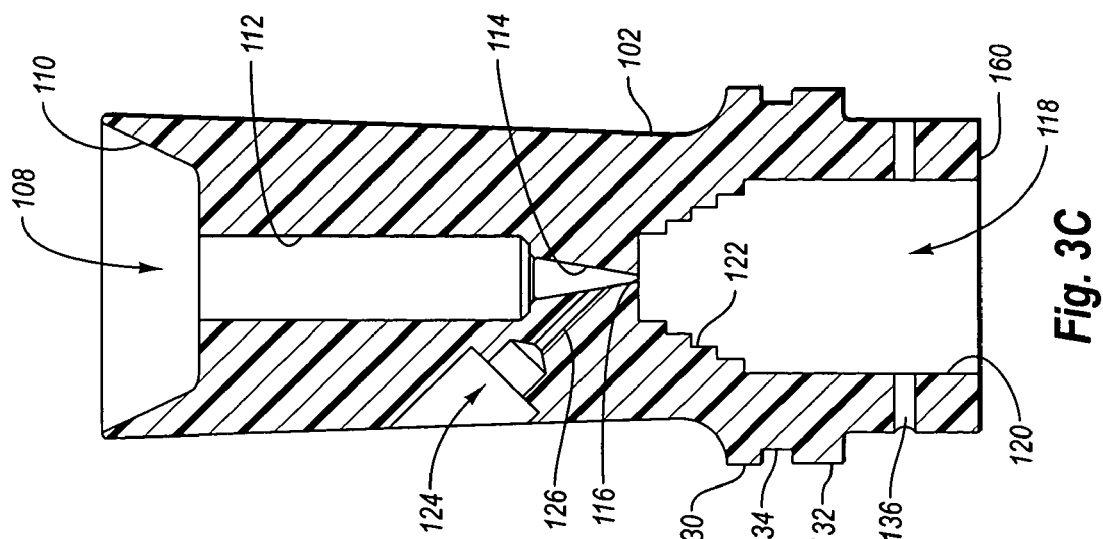
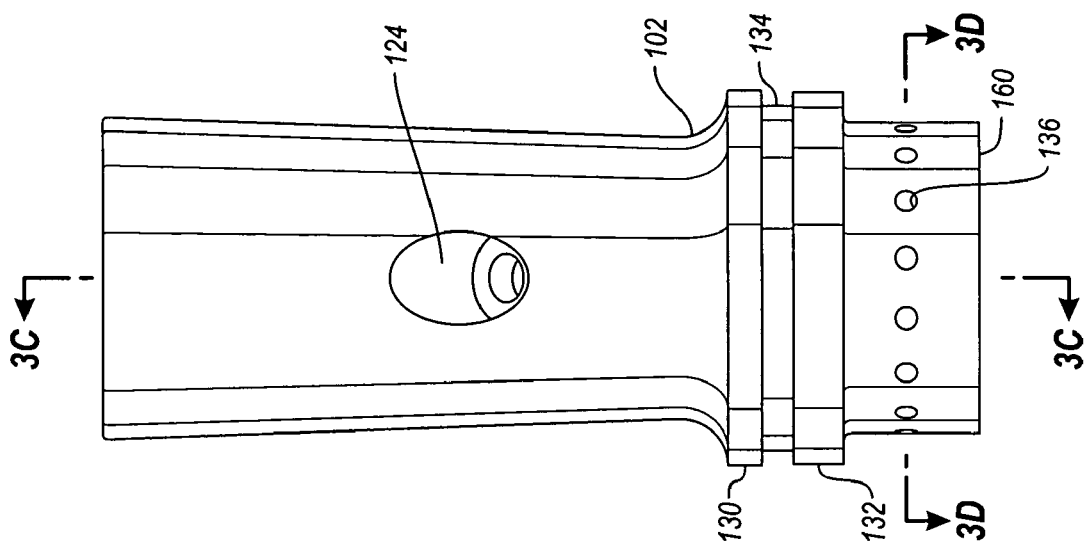
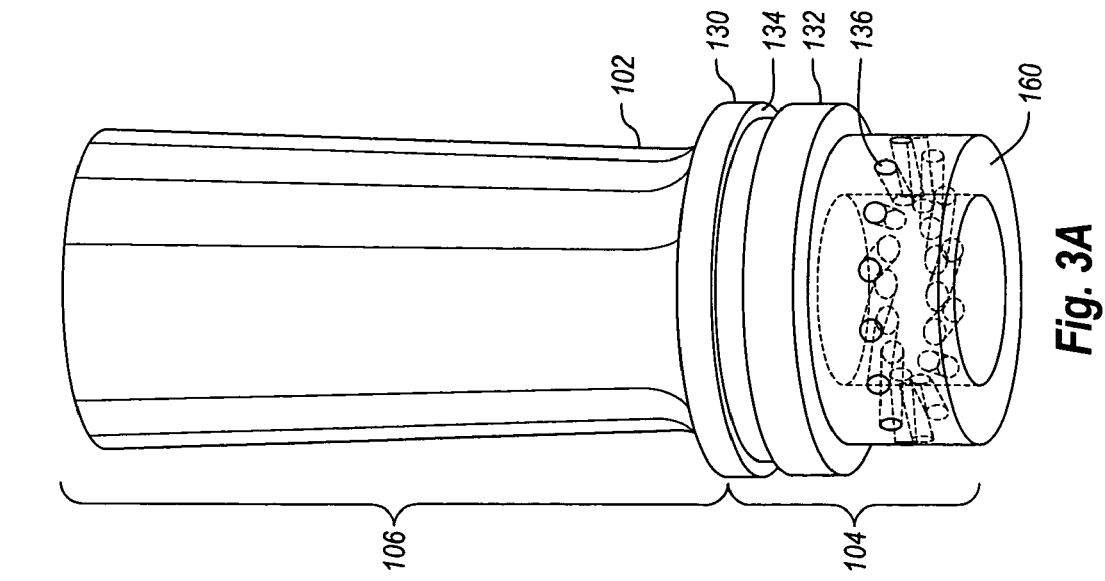

MEDICAL LIQUID PROCESSOR APPARATUS AND METHOD

FIELD OF THE INVENTION

This invention relates to fluid vaporizing and homogenizing devices and methods. More particularly, this invention relates to medical devices, systems, and methods for producing finely homogenized or vaporized gas-phase fluid mixtures.

BACKGROUND OF THE INVENTION

Many types of devices have been developed over the years for the purpose of converting liquids or aerosols into gas-phase fluids. Some such devices have been developed, for example, to discharge small droplets from an inhaler-type medicinal administration apparatus.

Typical inhalers include a pressurized canister with measured doses of medication inside. Squeezing the top of the canister converts liquid medication into an inhalable mist. Inhalers enable children and adults to deliver medicine directly to their lungs. Typical aerosol inhalers usually comprise a diverging nozzle at an outlet to the pressurized liquid, which tends to vaporize the liquid medicine to a droplet volume median diameter on the order of 50 μm.

50 μm particles produced by typical inhalers can effectively treat certain lung ailments. For example, bronchodilators such as albuterol treat acute asthma by causing the lung passages to open or dilate. Similarly, nebulizers typically vaporize liquid medications to a droplet volume median diameter on the order of 50 μm. However, in addition to direct lung treatments, applicant notes that liquid medicinal drugs could also be delivered directly to the bloodstream through the lungs.

The lungs include groups of tiny air sacs called alveoli. The alveoli have very thin walls or membranes, and small blood vessels called capillaries run through these membranes. Oxygen molecules are small enough to pass through the membranes and into the blood in the capillaries. Other particles having diameters of approximately 1 to 3 μm or smaller may also pass through the alveoli membranes and directly into the blood stream. Nevertheless, there are currently no efficient methods of reducing liquids to particle sizes small enough to pass through the alveoli membranes.

In addition, typical aerosol inhalers produce a wide range of particle droplet sizes, and much of the metered medication tends to simply impinge the mouth or the back of the throat of a user. Consequently, sometimes only a fraction of the medication is deeply inhaled.

SUMMARY OF THE INVENTION

The principles described herein may address some of the above-described deficiencies and others. Specifically, some of the principles described herein relate to liquid processor apparatuses and methods, some embodiments of which may be suited for medical applications.

One aspect provides a method comprising introducing a supply of liquid into a vortex, and breaking down the supply of liquid to a particle size of approximately 20 μm in diameter or smaller. According to one aspect, the method comprises breaking down a majority of the supply of liquid to a particle size of approximately 10 μm in diameter or smaller. According to one aspect, the method comprises breaking down a majority of the supply of liquid to a particle size of approximately 2 μm in diameter or smaller. In one aspect, the method comprises delivering the supply of liquid orally to a patient.

According to one aspect, introducing the supply of liquid comprises introducing a supply of liquid medication into the vortex. One aspect may further comprise supplying a pressurized air supply into a vortex chamber, where introducing the supply of liquid comprises pressurizing the liquid above a threshold pressure needed to open a biased valve leading to the vortex chamber. One aspect of the method may further comprise adjusting flow rate capacity of the supply of liquid into the vortex by changing a position of a needle valve stop. According to one aspect, breaking down the supply of liquid comprises processing at least 0.8 ml of fluid medicine per minute at an air flow rate of approximately five cubic feet per minute.

One aspect comprises a method of delivering liquid medication to a patient. The method comprises providing a mass of liquid medication, introducing the mass of liquid medication to a vortex, and breaking down a majority of the mass of liquid medication to a particle size of approximately 1-3 μm in diameter or smaller, and inhaling the mass of liquid medication. Introducing the liquid medication may comprise inserting the mass of liquid medication at a pressure sufficient to open a needle valve leading to the vortex. According to one aspect, the method may further comprise passing at least a portion of the mass of liquid medication directly into a patient's bloodstream by crossing an alveoli membrane of a patient's lungs.

One aspect comprises a method of delivering a medicinal liquid drug to a patient. The method comprises passing the medicinal liquid drug directly into a patient's bloodstream by crossing an alveoli membrane of the patients' lungs. According to one aspect, passing the medicinal liquid drug directly into a patient's bloodstream comprises introducing the medicinal liquid drug to an air vortex, vaporizing the medicinal liquid drug with the air vortex, diffusing the vaporized medicinal liquid drug, and causing the vaporized medicinal liquid drug to be inhaled into the patient's lungs.

One embodiment comprises a medicinal liquid drug delivery device. The medicinal liquid drug delivery device comprises a body, a mouthpiece attached directly or indirectly to the body, a vortex chamber disposed inside the body, a medicinal liquid drug port, and a valve between the medicinal liquid drug port and the vortex chamber. The valve may comprise a biased needle valve for allowing and preventing fluid communication between the vortex chamber and the medicinal liquid drug port. The apparatus may further comprise a linearly adjustable stop abutting the biased needle valve. The stop may comprise a micrometer abutting the biased needle valve, the micrometer adjustably limiting a range of linear travel of the biased needle valve.

According to one embodiment, the vortex chamber comprises an vertex, and the valve comprises a needle valve at and opposite of the vertex. According to one embodiment, the apparatus further comprises a diverging nozzle disposed in the body, and the vortex chamber is defined by a tapering annulus between the body and the diverging nozzle. The vortex chamber may comprise a stepped outer surface. One embodiment of the apparatus further comprises an air ring arranged around the body, an air ring conduit between the air ring and the body, and a plurality of angled flow passages disposed in the body and leading to the vortex chamber. The apparatus may include a compressed air port disposed in the air ring.

According to one embodiment, the apparatus further comprises a pressurized air supply in fluid communication with the vortex chamber, and the valve is biased to open at a pressure of no less than approximately five to twenty PSI above a pressure of the pressurized air supply.

One aspect provides a vortex system for nebulizing a liquid for inhalation. The vortex system comprises a vortex chamber for mixing the liquid with a gas in a vortex, the vortex chamber comprising a vertex. The vortex system may also comprise a liquid inlet arranged at the vertex of the vortex chamber, and a diffuser arranged interior to and in fluid communication with the vortex chamber for receiving a mixture of liquid and gas from the vortex. According to one embodiment, the vortex system includes a valve for selectively allowing the liquid through the liquid inlet. One embodiment of the vortex system may further comprise a gas ring around the vortex chamber, the vortex chamber comprising a plurality of angled passages in fluid communication with the gas ring. The gas ring may be in fluid communication with a gas supply pressurized to at least fifty PSI.

Another embodiment provides a medicinal drug delivery device comprising an inner nozzle having an axis, a vortex chamber jacketing at least a portion of the inner nozzle (the vortex chamber being coaxial with the axis), a mouthpiece at least partially housing the inner nozzle, a linear valve at a common vertex of the inner nozzle and the vortex chamber, and a drug introduction port in fluid communication with the linear valve. One embodiment of the medicinal drug delivery device further comprises an adjustable stop to the linear valve.

BRIEF DESCRIPTION OF THE DRAWINGS

The accompanying drawings illustrate certain embodiments discussed below and are a part of the specification.

FIG. 2A is a side view of an internal nozzle of the medical shown in FIG. 1.

FIG. 2B is a cross section of the internal nozzle of FIG. 2A.

FIG. 3A is a perspective view of a body of the medical drug delivery shown in FIG. 1.

FIG. 3B is a side view of the body shown in FIG. 3A.

FIG. 3C is a cross-section of the body shown in FIG. 3B, taken along line 3C-3C.

Throughout the drawings, identical reference characters and descriptions indicate similar, but not necessarily identical elements.

DETAILED DESCRIPTION OF THE PREFERRED EMBODIMENTS

Illustrative embodiments and aspects are described below. It will of course be appreciated that in the development of any such actual embodiment, numerous implementation-specific decisions must be made to achieve the developers' specific goals, such as compliance with system-related and business-related constraints, that will vary from one implementation to another. Moreover, it will be appreciated that such a development effort might be complex and time-consuming, but would nevertheless be a routine undertaking for those of ordinary skill in the art having the benefit of this disclosure.

As used throughout the specification and claims, the terms "medicine" or "medication" refer to a drug that treats, prevents, or alleviates the symptoms of disease and also includes dietary supplements and nutraceuticals. The words "including" and "having," as used in the specification, including the claims, have the same meaning as the word "comprising."

Figure 1:
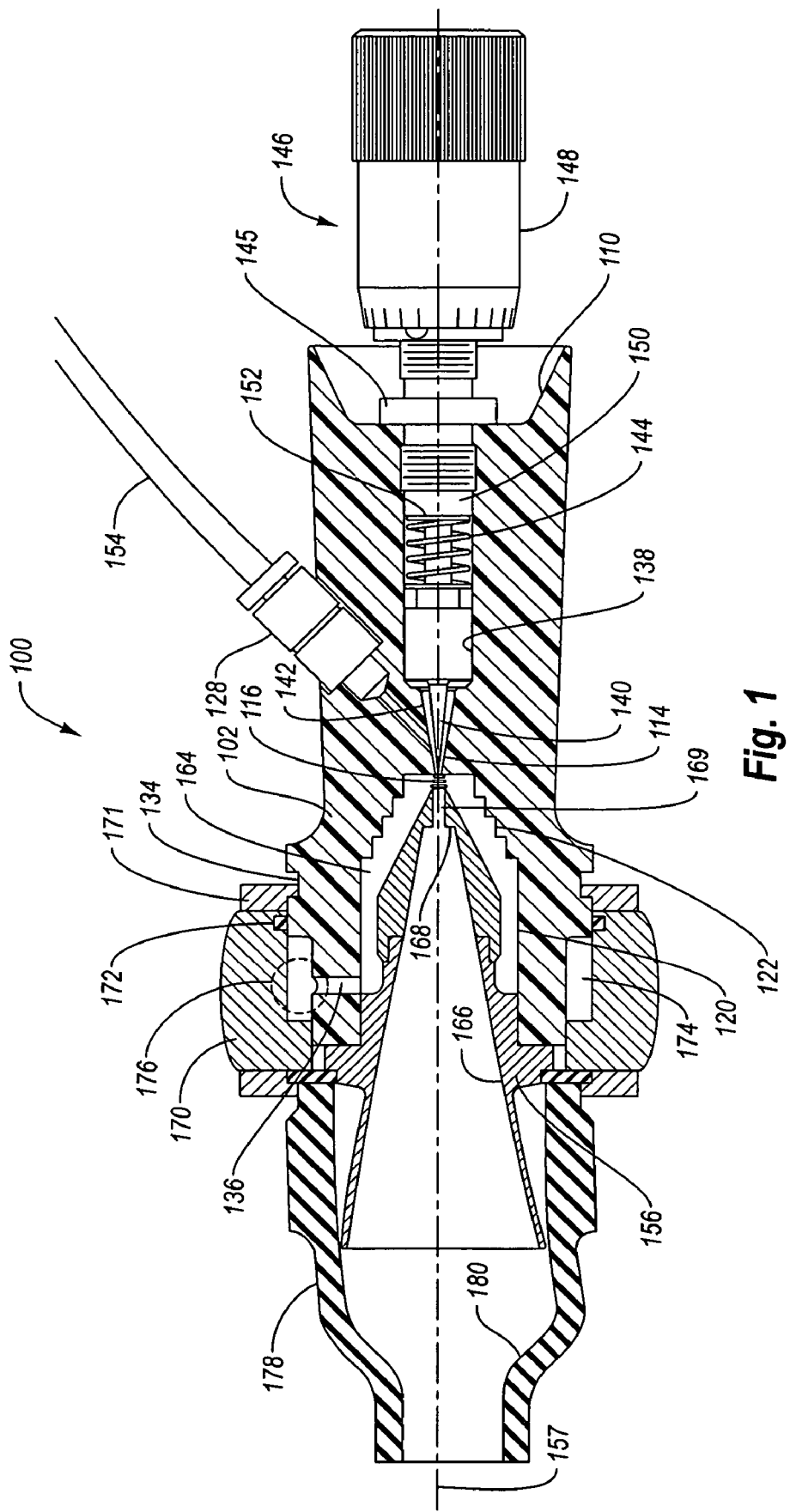
FIG. 1 is an assembled cross sectional view of a medical drug delivery apparatus according to one aspect.

Turning now to the figures, and in particular to FIG. 1, one embodiment of a vortex system is shown. The vortex system may comprise, for example, a liquid delivery device. The liquid delivery device may prepare a variety of liquids for inhalation. For example, the liquid delivery device may prepare liquids including, but not limited to, medicinal drugs, supplements, nutraceuticals, or other liquids. According to one aspect, the liquid delivery device is a medicinal drug delivery device 100. The medicinal drug delivery device 100 may be used, for example, to vaporize or nebulize and deliver a fluid or liquid, such as a liquid drug, directly to a bloodstream of a patient without an injection. The medicinal drug delivery device 100 may generate a gaseous, homogenous mixture of medication and air that can be inhaled, with medication particles small enough pass through the membranes of the patient's alveoli and directly into the bloodstream.

The medicinal drug delivery device 100 may create the gaseous, homogenous mixture of medication and air by introducing fluid or liquid medication to a vortex. The vortex pulverizes and vaporizes liquid medication into very small particles or droplets that can pass through alveoli membranes. However, the vortex of the medicinal drug delivery device 100 may also create larger particles that will not pass though the alveoli membranes of a patient, depending on the configuration and/or parameters of the medicinal drug delivery device 100.

Figure 3D:
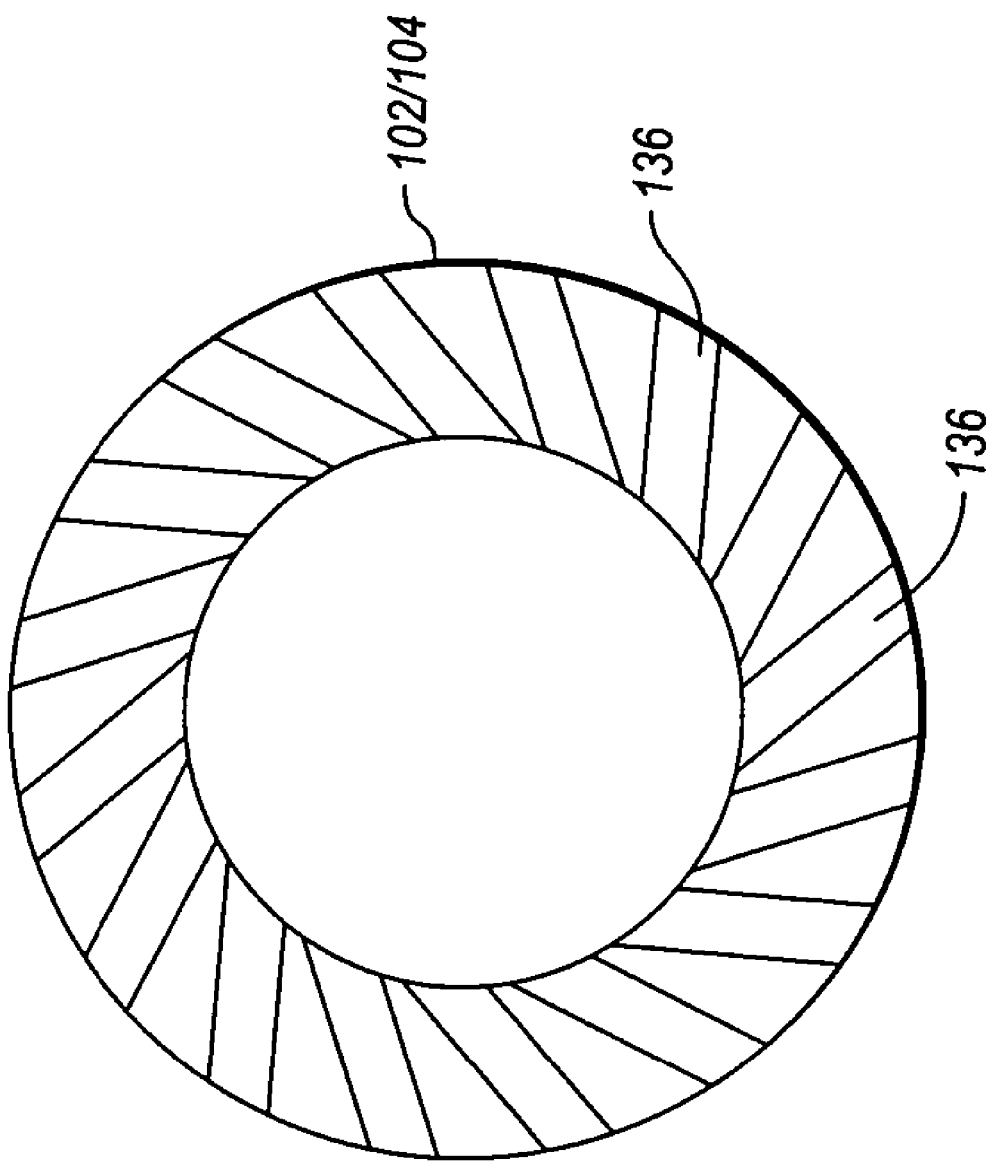
FIG. 3D is a cross-section of the body shown in FIG. 3B, taken along line 3D-3D.

As shown in the embodiment of FIG. 1, the medicinal drug delivery device 100 includes a body 102. The body 102 may comprise any rigid material, including, but not limited to, plastic, metal, composites, and ceramics. The body 102 may comprise any shape, such as the generally cylindrical shape shown. The body is shown in detail in FIGS. 3A-3D. As shown in FIGS. 3A-3C, the body 102 may comprise a head portion 104 and a tail portion 106. The tail portion 106 may be elongated and cylindrical, with a first internal cavity 108. According to one embodiment, the first internal cavity 108 comprises multiple diameters. For example, the first internal cavity 108 may include a tapered dish portion 110 leading to an internal cylindrical recess 112. The internal cylindrical recess 112 may lead to a converging cone 114 that may comprise a fluid or liquid inlet. A vertex 116 of the cone 114 may be open to a second internal cavity 118 of the body 102.

The second internal cavity 118 of the body 102 may comprise a generally cylindrical inner wall 120 and a tapered inner wall 122. The tapered inner wall 122 may comprise a plurality of stairs as shown in FIG. 3C that step inward toward the vertex 116 of the cone 114.

According to one embodiment, the body 102 includes a side or angled port 124 disposed in the tail portion 106. The angled port 124 may comprise a medicinal liquid drug port which is in fluid communication with the first internal cavity 108. In one embodiment, a liquid passageway 126 of the angled port 124 is open to the converging cone 114 of the first internal cavity 108. Although the angled port 124 forms an acute angle with the body 102 in FIGS. 1 and 3C, this is not necessarily so. The angled port 124 may take on any shape, angle, and form, including, for example, an orientation normal to the body 102.

The head portion 104 of the body 102 may include a number of features. For example, one embodiment includes a pair of external protruding rings 130, 132 flanking a recess 134. The rings 130, 132 and the recess 134 may facilitate attachment of the body 102 to other components.

According to one embodiment, the head portion 104 includes a plurality of angled passages 136 extending from the exterior of the body 102 into the second internal cavity 118. As shown in FIG. 3D, the angled passages 136 are angled from normal, and are not perfectly tangential. The angled passages 136 may be angled, for example, between five and seventy-five degrees from tangent. Air or other fluid flowing into the angled passages 136 may create a vortex inside the body 102 as described below.

According to one embodiment, the first internal cavity 108 of the body 102 receives a valve. For example, as shown in FIG. 1, a biased linear or needle valve 138 extends from the internal cylindrical recess 112 (FIG. 3C) into the converging cone 114. A tapered tip 140 of the needle valve 138 is sized to provide an annulus 142 between the converging cone 114 and the tapered tip 140, and the annulus 142 is in fluid communication with the with the angled port 124. The tapered tip 140 is biased into the converging cone 114 to seal off the vertex 116 and close fluid communication through the cone 114. A spring 144 may bias the needle valve 138 into a closed position.

According to one embodiment, the needle valve 138 abuts a stop, which limits the linear travel range of the needle valve 138. The stop may be adjustable, and may comprise, for example, a micrometer 146. The micrometer 146 may extend through a flange 145 mounted in the dish portion 110 of the first internal recess 108 (FIG. 3C). Rotation of a knob 148 of the micrometer 146 causes linear movement of a pin 150 of the micrometer 146. The pin 150 of the micrometer 146 provides a surface abutting the spring 144, and also provides a hard stop against further valve opening when an end 152 of the needle valve 138 comes into contact therewith. Therefore, the micrometer 146 may be adjusted to precisely limit the travel extents of the needle valve 138. It may be desirable to finely adjust the linear travel limits of the needle valve 138 to control the amount of fluid that may pass through the cone 114 when the needle valve 138 opens.

According to one embodiment, the angled port 124 in the body 102 may be receptive of a fitting, such as a quick touch fitting 128 illustrated in FIG. 1. The quick touch fitting 128 is connected to a medicine supply conduit 154. The spring 144 of the needle valve 138 may be biased to remain closed until a predetermined pressure threshold is reached. Accordingly, a certain pressure level from, for example, the medicine supply conduit 154, must be reached to inject a mass of medicine out through the cone 114. According to some embodiments, a pressure of at least five to fifty PSI above normal conditions (the pressure the tapered tip 140 is normally exposed to, which may be above atmospheric) may be selectively supplied from the medicine supply conduit 154 to open the needle valve 138.

According to one embodiment, the second internal cavity 118 (FIG. 3C) of the body 102 may receive a diffuser such as a nozzle 156. The nozzle 156 is at least partially disposed inside the second internal cavity 118 (FIG. 3C). The nozzle 156 is shown in a side view in FIG. 2A and in cross-section in FIGS. 1 and 2B. The nozzle 156 includes an axis 157 and an outer rim 158 that may bear against and attach to an end wall 160 (FIG. 3A) of the body 102 (FIG. 3A). A step down diameter 162 of the nozzle 156 may be sized to fit snugly within the cylindrical inner wall 120 (FIG. 3C) of the body 102 (FIG. 3C). The step down diameter 162 does not, however, insert past the angled passages 136 (FIGS. 1 and 3C) and may be approximately tangent with the angled passages 136 (FIGS. 1 and 3C). As shown in FIG. 1, the outer surface of the nozzle 156 may neck down to create an annulus 164 with the cylindrical inner wall 120 and the tapered inner wall 122.

According to one embodiment, the annulus 164 between the body 102 and the nozzle 156 defines a vortex chamber with a vertex at the approximate same location as the vertex 116 of the cone 114. The vortex chamber may thus jacket at least a portion of the nozzle 156 and be coaxial with the nozzle 156. The angled passages 136 in the body 102 lead to the vortex chamber comprising the annulus 164. A supply of air or other fluid entering through the angled passages 136 in the body 102 tends to create a vortex in the vortex chamber.

The inside of the nozzle 156 may comprise a continuous or discontinuous diffuser. For example, as shown in FIGS. 1 and 2B, the inside of the nozzle 156 may comprise taper 166 with a discontinuity 168. At the discontinuity 168, the inside of the nozzle 156 may comprise a passage 169 of generally constant diameter. The passage 169 is adjacent to the vertex 116 of the cone 114, and is open to the vertex 116. The passage 169 is thus in fluid communication with the vortex chamber or annulus 164. According to one embodiment, there is a gap of approximately 0.067 inches between the nozzle 156 and the cone 114.

According to one embodiment, there is a gas or air ring 170 arranged around the head portion 104 (FIG. 3A) of the body 102. The air ring 170 may include a flange or lip 171 that fits into the recess 134 of the body 102. One or more O-rings 172 may seal between the body 102 and the air ring 170. An annulus between the air ring 170 and body 102 forms an air ring conduit 174 in fluid communication with the angled passages 136 and thus the vortex chamber. The air ring 170 may include a pressurized air port 176 connected to a pressurized air or gas source.

According to one embodiment, the body 102 is attached directly or indirectly to a mouthpiece 178. According to the embodiment of FIG. 1, the mouthpiece 178 attaches to the air ring 170 and/or the nozzle 156. The mouthpiece 178 may enclose a portion of the nozzle 156 that extends outside of the body 102. The mouthpiece 178 may comprise a converging section 180 to direct flow to a patient or other user. However, according to some embodiments, the mouthpiece 178 is omitted and the nozzle 156 may comprise a mouthpiece.

According to one aspect, embodiments described herein and others may be used to prepare liquids for users. For example, embodiments may be used to prepare liquid medication for a patient. Accordingly, a supply of fluid or liquid medicine may be introduced into a vortex to create a gaseous, homogenous liquid or liquid medicine supply having a very small particle diameter. According to one aspect, compressed or pressurized air is introduced into the air ring conduit 174 through the pressurized air port 176. The pressurized air in the air ring conduit 174 is forced through the angled passages 136 into the vortex chamber (defined, for example, by the annulus 164). The angled passages 136 cause the pressurized air to form a high speed vortex in the vortex chamber. The energy level of the vortex in the vortex chamber may be adjusted by adjusting the pressure and/or flow rate of gas into the air ring conduit 174. According to one aspect, air pressurized to approximately fifty to one hundred PSI is supplied to the air ring 170.

According to one aspect, pressurized air enters the vortex chamber and creates a vortex. Further, a supply of liquid medication is introduced to the vortex. In one aspect, liquid such as liquid medication is pressurized to a predetermined threshold level higher than the pressure of the pressurized air. For example, the spring 144 of the needle valve 138 may be set to open upon the application of fifty-five to seventy five PSI. Accordingly, the medication may be pressurized five to twenty-five PSI greater than the pressurized air. The pressure of the liquid medication opens the needle valve 138 and allows the liquid medication to exit the cone 114 into the vortex chamber. The vortex of the vortex chamber quickly breaks down and pulverizes the liquid medication into small, gaseous particles. According to one embodiment, the vortex breaks part or a majority of the liquid medication down to a particle size of no more than ten to twenty μm. A particle size of no more than ten μm can be deeply inhaled to treat lung ailments. The supply of vaporized medication mixed with air exits the vortex chamber through the nozzle 156, where it is diffused for oral inhalation by a patient through the mouthpiece 178.

According to some aspects, it may be desirable to pass a mass of liquid medication directly into a patient's bloodstream by crossing the alveoli membrane of a patient's lungs. Therefore, according to some aspects, the vortex in the vortex chamber may be sufficiently energized to break down liquid medication to particle sizes of no greater than approximately 1.0 to 3.0 μm in diameter. According to some aspects, providing a supply of air to the vortex chamber at approximately fifty to one hundred PSI and delivering the air at approximately five CFM breaks down a majority of liquid medicines provided at a rate of approximately 0.8 ml/min to a particle diameter of no more than 1.0 to 3.0 μm. According to some aspects, 95% of liquid medicine supplied to the vortex chamber is broken down to a particle diameter of no more than 1.0 to 3.0 μm. Particles having a diameter of no more than approximately 1.0 to 3.0 μm can pass through the alveoli membranes of the lungs and directly into the patient's blood stream. Accordingly, inhalation of liquid medicine processed according to the principles described herein effectively delivers liquid medication to a patient without needles or digestion. Therefore, one can deliver medication to a patient according to principles described herein by passing a medicinal liquid drug directly into a patient's bloodstream by crossing the membrane of the alveoli of the lungs. Flow rates of the vortex air and the fluid or liquid medicine supply may be adjusted by those of skill in the art having the benefit of this disclosure to generate any desired medicine particle size. The flow rate of the liquid medicine introduced to the vortex may be adjusted, for example, by changing the position of the micrometer 146, which in turn control how far the needle valve 138 opens.

The preceding description has been presented only to illustrate and describe certain aspects, embodiments, and examples of the principles claimed below. It is not intended to be exhaustive or to limit the described principles to any precise form disclosed. Many modifications and variations are possible in light of the above teaching. Such modifications are contemplated by the inventor and within the scope of the claims. The scope of the principles described is defined by the following claims.

What is claimed is:

1. A method of preparing medication for inhalation, comprising:
   providing a medication delivery device that includes a body and a nozzle, the body including a first end having a first converging chamber defined therein and a second end having a second converging chamber defined therein, a vertex of the first converging chamber intersecting with a vertex of the second converging chamber, a portion of the nozzle positioned in the second converging chamber, a vortex chamber being defined between the nozzle and a surface of the second converging chamber, the nozzle defining a nozzle passage along a central axis thereof that is open adjacent to the vertex of the second converging chamber;
   introducing a supply of air in the vortex chamber to create a vortex flow;
   introducing a supply of liquid medicine through the first converging chamber into the vortex flow at the vertex of the second converging chamber;
   breaking down the supply of liquid medicine to a particle size of approximately 20 micrometers in diameter or smaller;
   delivering a mixture of the supply of air and the supply of liquid medicine having a particle size of 20 micrometers in diameter or smaller through the nozzle passage and out of the medication delivery device.

2. A method according to claim 1, further comprising breaking down a majority of the supply of liquid medicine to a particle size of approximately 10 micrometers in diameter or smaller.

3. A method according to claim 1, further comprising breaking down a majority of the supply of liquid medicine to a particle size of approximately 2 micrometers in diameter or smaller.

4. A method according to claim 1, further comprising delivering the supply of liquid medicine orally to a patient.

5. A method according to claim 1 wherein the introducing the supply of liquid medicine comprises introducing a supply of liquid medication to the vortex.

6. A method according to claim 1, further comprising supplying a pressurized air supply into a vortex chamber;
   wherein the medication delivery device further includes a valve positioned in the first converging chamber and biased into a closed positioned;
   wherein the introducing the supply of liquid medicine comprises pressurizing the liquid medicine above a threshold pressure needed to open the valve leading to the vortex chamber.

7. A method according to claim 1, further comprising adjusting flow rate capacity of the supply of liquid medicine into the vortex by changing a position of a needle valve stop.

8. A method according to claim 1 wherein the breaking down comprises processing at least 0.8 ml of liquid medicine per minute.

9. A method of delivering a medicinal liquid drug to a patient, comprising:
   passing the medicinal liquid drug directly into a patient's bloodstream by crossing an alveoli membrane of the patient's lungs;
   wherein the passing the medicinal liquid drug directly into a patient's bloodstream comprises:
   providing a medication delivery device that includes a body and a nozzle, the body including a first end having a first converging chamber defined therein and a second end having a second converging chamber defined therein, a vertex of the first converging chamber intersecting with a vertex of the second converging chamber, a portion of the nozzle positioned in the second converging chamber, a vortex chamber being defined between the nozzle and a surface of the second converging chamber, the nozzle defining a nozzle passage along a central axis thereof that is open adjacent to the vertex of the second converging chamber;
   introducing a supply of air in the vortex chamber to create a vortex flow;
   introducing a supply of liguid medicine ton through the first converging chamber into the vortex flow at the vertex of the second converging chamber;
   causing the vaporized medicinal liquid drug to be inhaled into the patient's lungs.

10. An apparatus, comprising:
    a medicinal liquid drug delivery device, the medicinal liquid drug delivery device comprising:
    a body;
    a mouthpiece attached to the body;

a vortex chamber disposed inside the body, the vortex chamber having a first end, a second end and a vertex;

a medicinal liquid drug port defined in the body;

a valve between the medicinal liquid drug port and the vortex chamber, the valve controlling flow of medicinal liquid drug at the first end of the vortex chamber and a vertex of the valve intersecting with the vertex of the vortex chamber;

a nozzle positioned in the vortex chamber, the nozzle including a channel, the channel being open at the first end of the vortex chamber, and having a vertex along the vertex of the vortex chamber;

at least one air supply inlet at the second end of the vortex chamber, the at least one air supply inlet providing flow of air into the vortex chamber to create a vortex flow in the vortex chamber;

wherein the channel is arranged and configured to accept a mixture of the air and the medicinal liquid drug into the channel at the first end of the vortex chamber.

11. An apparatus according to claim 10 wherein the valve comprises a biased needle valve for allowing and preventing fluid communication between the vortex chamber and the medicinal liquid drug port.

12. An apparatus according to claim 10 wherein the valve comprises a biased needle valve for allowing and preventing fluid communication between the vortex chamber and the medicinal liquid drug port; and further comprising a linearly adjustable stop abutting the biased needle valve.

13. An apparatus according to claim 10 wherein the valve comprises a biased needle valve for allowing and preventing fluid communication between the vortex chamber and the medicinal liquid drug port; and further comprising a micrometer abutting the biased needle valve, the micrometer adjustably limiting a range of linear travel of the biased needle valve.

14. An apparatus according to claim 10 wherein the vortex chamber comprises a vertex, wherein the valve comprises a needle valve at the vertex.

15. An apparatus according to claim 10, wherein the vortex chamber is defined by an annulus between the body and the nozzle, and the nozzle includes a diverging portion.

16. An apparatus according to claim 10 wherein the vortex chamber comprises a stepped outer surface and the channel comprises a stepped surface.

17. An apparatus according to claim 10, further comprising:

an air ring arranged around the body;

an air ring conduit between the air ring and the body;

a plurality of angled flow passages disposed in the body and leading to the vortex chamber through the at least one air supply inlet.

18. An apparatus according to claim 10, further comprising:

an air ring arranged around the body;

an air ring conduit between the air ring and the body;

a plurality of angled flow passages disposed in the body and leading to the vortex chamber through the at least one air supply inlet;

a compressed air port disposed in the air ring.

19. An apparatus according to claim 10, further comprising:

a pressurized air supply in fluid communication with the vortex chamber through the at least one air supply inlet;

wherein the valve is biased to open at a pressure of no less than approximately five PSI above a pressure of the pressurized air supply.

20. An apparatus according to claim 10, further comprising:

a pressurized air supply in fluid communication with the vortex chamber through the at least one air supply inlet;

wherein the valve is biased to open at a pressure of no less than approximately twenty PSI above a pressure of the pressurized air supply.

21. A vortex system for nebulizing a liquid for inhalation, comprising:

a vortex chamber for mixing the liquid with a gas in a vortex, the vortex chamber comprising a vertex, a first end and a second end;

a liquid inlet arranged at the first end and vertex of the vortex chamber;

a gas ring around the second end of the vortex chamber, the vortex chamber comprising a plurality of angled passages in fluid communication with the gas ring, the vortex chamber being configured to receive a gas supply that is pressurized to at least fifty PSI through the gas ring and plurality of angled passages;

a diffuser arranged radially interior to and in fluid communication with the vortex chamber, the diffuser including a channel having an opening at the first end of the vortex chamber and adjacent to the vertex for receiving a mixture of liquid and gas from the vortex;

a valve for variably allowing the liquid through the liquid inlet.

22. A vortex system according to claim 21 wherein the valve comprises a biased needle valve.

\* \* \* \* \*